United States Patent [19]

Malmin

[11] 3,949,748

[45] Apr. 13, 1976

[54] INJECTION SYRINGE HAVING ASPIRATING AND METERING CAPABILITIES

[76] Inventor: Oscar Malmin, 127 E. Wayne Ave., Akron, Ohio 44301

[22] Filed: Sept. 26, 1974

[21] Appl. No.: 509,423

[52] U.S. Cl. ........ 128/218 DA; 128/218 C; 32/40 R
[51] Int. Cl.² ......................................... A61M 5/00
[58] Field of Search ............ 128/213, 214 R, 214 E, 128/215, 216, 218 R, 218 P, 218 PA, 218 DA, 218 G, 218 C, 218 D, 218 F, 234, 276, 278, 347; 32/22, 40 R; 222/390

[56] References Cited
UNITED STATES PATENTS

| | | | |
|---|---|---|---|
| 1,718,596 | 6/1929 | Smith | 128/218 D |
| 2,345,875 | 4/1944 | James et al. | 128/276 |
| 2,564,977 | 8/1951 | Hu | 128/276 |
| 2,624,338 | 1/1953 | Moore et al. | 128/218 D |
| 2,737,949 | 3/1956 | Brown | 128/218 D |
| 2,904,044 | 9/1959 | Jalar et al. | 128/218 DA |
| 3,051,172 | 8/1962 | Bruchhaus | 128/218 DA |
| 3,110,310 | 11/1963 | Cislak | 128/218 C |
| 3,727,614 | 4/1973 | Kniazuk | 128/218 G |
| 3,838,690 | 10/1974 | Friedman | 128/218 DA |

FOREIGN PATENTS OR APPLICATIONS

| | | | |
|---|---|---|---|
| 137,660 | 1903 | Germany | 128/276 |
| 16,859 | 1934 | Australia | 128/213 |

Primary Examiner—John D. Yasko
Attorney, Agent, or Firm—Freeman & Taylor

[57] ABSTRACT

An improved cartridge type syringe capable of being utilized as an anesthetic injector, root canal irrigator, and periodontal pocket irrigator is disclosed which has an aspirating capability as well as a metering capability to measure and control the amount of material injected. The syringe includes means for locating the cartridge within the barrel of the syringe to provide a sealed area adjacent the needle for aspiration purposes. It also includes a means for controlling the amount and rate of flow of the material being injected by utilizing a spring-loaded plunger, a detent carrying drive shaft, and gripping means which are capable of gripping the detents on the drive shaft. The device is constructed so that upon depression of the spring-loaded plunger, the rear seal of the cartridge will be pushed forward a predetermined distance by the drive shaft so as to inject a measured amount of fluid. Upon release of the plunger the spring will return the plunger to its normal position, with the gripping means holding the drive shaft in place. Further repeated depression and release of the plunger will advance the drive shaft the distance of one detent in each case, thereby insuring that only a predetermined amount of liquid is injected at a time.

9 Claims, 7 Drawing Figures

INJECTION SYRINGE HAVING ASPIRATING AND METERING CAPABILITIES

BACKGROUND OF THE INVENTION

This invention in general relates to syringes which are capable of carrying disposable cartridges which may contain local anesthetics, irrigating fluids or, for that matter, virtually any type of injectable material. The invention specifically relates to a syringe which is capable of providing a pocket adjacent the needle which is completely sealed and joined to a suction means for aspirating purposes and also providing means for measuring and controlling the amount of fluid injected from the cartridge.

DESCRIPTION OF THE PRIOR ART

The following patent prior art is known to applicant:

| | | |
|---|---|---|
| Richards | U.S. Patent | 375,427 |
| Hale | U.S. Patent | 881,469 |
| Quintin | U.S. Patent | 1,189,735 |
| Hagemeier | U.S. Patent | 2,102,591 |
| Melott | U.S. Patent | 3,224,445 |
| Cheney | U.S. Patent | 3,685,514 |
| Shields | U.S. Patent | 3,768,473 |
| Schmidt | U.S. Patent | 3,797,487 |
| Malmin | U.S. Patent | 3.807,048 |
| Cimber | U.S. Patent | 3,809,095 |
| Sarnoff | U.S. Patent | 3,811,441 |
| Malmin | U.S. Patent | 3,816,921 |
| Baker | U.S. Patent | 3,727,310 |

In addition to the aforementioned patent prior art, Applicant is aware of conventional syringes which are readily available on the market and which rely on retracting the rear rubber seal of the cartridge by means of a barbed hook on the plunger, with a consequent distortion of the rubber seal. This can cause, on the outward movement of the plunger, blood to be drawn into the cartridge and further restricts the use of syringes to large gauge needles. The presently available syringes also require the operator's hand to be spread to obtain retraction of the rubber stopper, which is both awkward and difficult to achieve. These are usually held between the index and middle fingers while the thumb is placed in a thumb ring on the plunger. To aspirate, it is necessary to pull the thumb backward which is awkward and also makes it difficult to hold the needle in position.

Additionally, the commonly available forms of injection syringes have no positive means of regulating the amount or rate of injection, with the consequent disadvantage of permitting the possibility of a completely uninterrupted flushing injection of the material which can have disastrous effects. There are no positive controls or checks known to Applicant to interrupt or regulate or control the rate and amount of flow.

SUMMARY OF THE INVENTION

It has been discovered that the aforementioned disadvantages can be overcome by providing an injection syringe which provides for sealing of the cartridge within the barrel of the syringe and locating it in a position so that a completely sealed chamber communicating with the needle and with the vacuum source is provided. This makes it possible to achieve a complete aspiration of the area in question without the danger of contaminating the contents of the cartridge.

It has also been discovered that the precise amount and rate of injection can be controlled by providing metering means which include a spring-loaded plunger and an associated drive shaft having detent means thereon. This type of drive shaft, due to the detent means and certain gripping means carried by the plunger, make it possible to inject only a predetermined amount of fluid into the patient on each depression of the plunger.

Means are also provided on the end of the drive shaft to engage the plug or seal in the rear end of the cartridge to overcome the necessary resistance of the back pull of the gripping fingers of the metering device, thereby maintaining engagement between the drive shaft and the rear cartridge seal.

Accordingly, production of an improved injection syringe of the type above-described becomes the principal object of this invention, with other objects thereof becoming more apparent upon a reading of the following brief specification, considered and interpreted in view of the accompanying drawings.

BRIEF DESCRIPTION OF THE PREFERRED EMBODIMENTS

Figure 1:
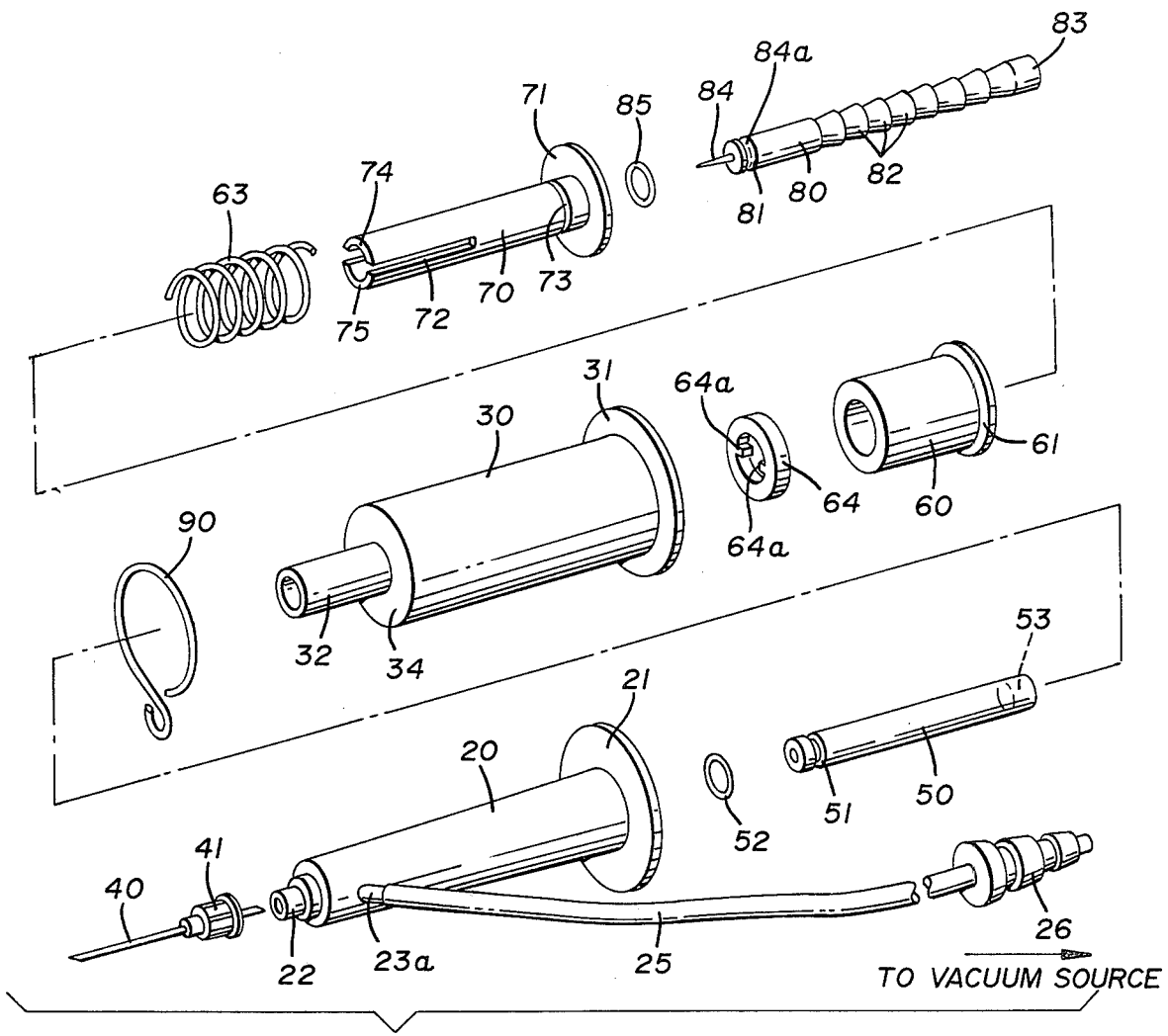
FIG. 1 is an exploded perspective view showing the various components of the syringe in unassembled condition.
Figure 3:
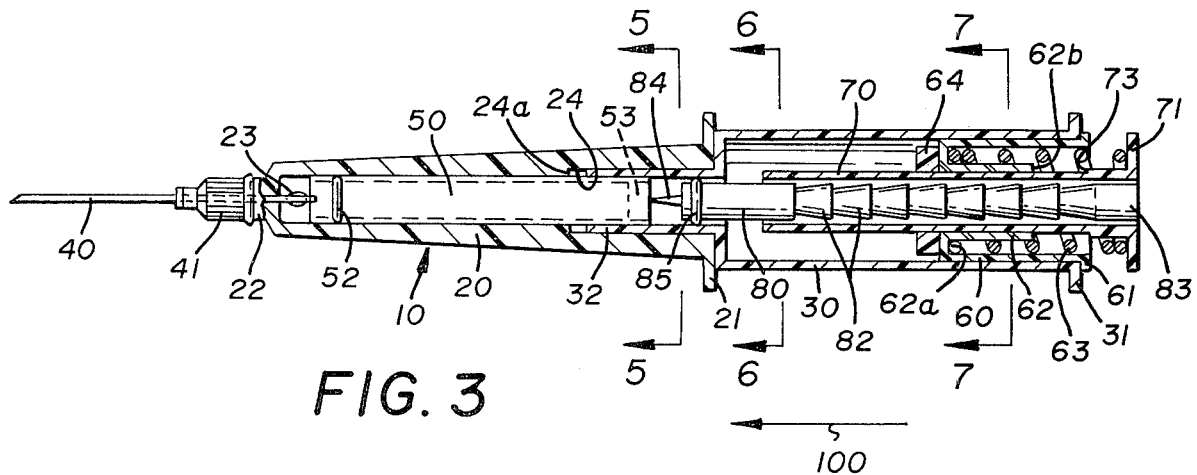
FIG. 3 is a sectional elevational view partially broken away and showing the assembled syringe prior to seating of the cartridge.
Figure 4:
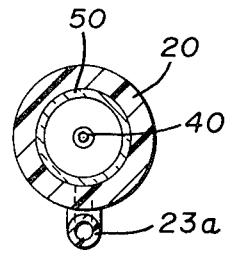
FIG. 4 is a sectional view taken along the lines 4—4 of FIG. 2.
Figure 5:
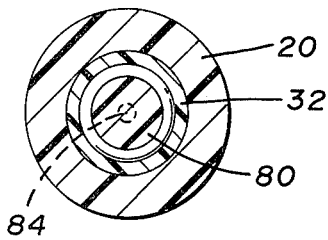
FIG. 5 is a sectional view taken along the lines 5—5 of FIG. 3.
Figure 6:
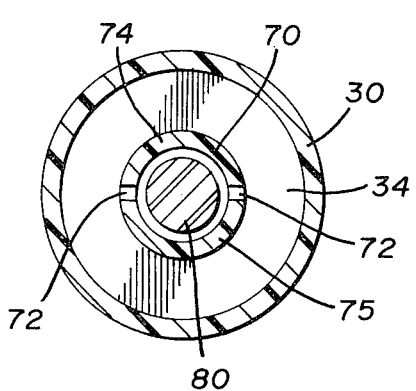
FIG. 6 is a sectional view taken along the lines 6—6 of FIG. 3.
Figure 7:
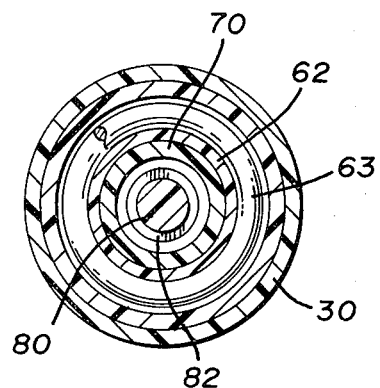
FIG. 7 is a sectional view taken along the lines 7—7 of FIG. 3.

Referring first then to FIGS. 1 and 3 for a general description of the device, it will be noted that the overall syringe, generally indicated by the numeral 10, includes a barrel 20, and a body 30. Received internally of the barrel 20 is a conventional cartridge 50, while a conventional double-ended needle 40 is received on the outboard end of the barrel 20. A spring housing 60 is provided which receives the plunger 70, which is in turn held in place by spring 63. Received within the plunger 70 is a detent type metering means or drive shaft 80.

Figure 2:
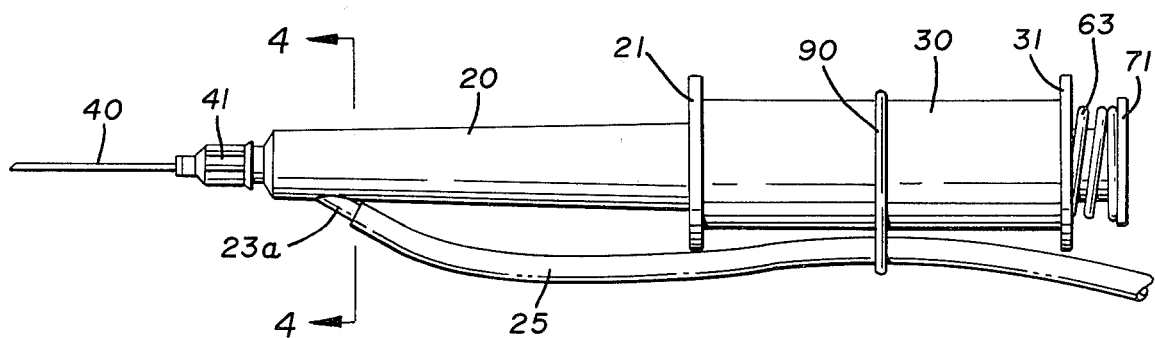
FIG. 2 is an elevational view showing the syringe in assembled condition.

Considering again FIGS. 1 and 2 for a more detailed description of the invention, it will be noted that the barrel 20 of the syringe 10 is an elongate, hollow, tapered member having a fitting 21 at one end thereof for reception of the needle 40 and the needle-carrying member 41. No detail has been shown with regard to this since there are a number of ways in which the needle can be attached to the end of the barrel, such as by threading, press fit, etc. Barrel 20 also has a circumferential flange 21 at its opposite end, with this flange being intended to be engaged by the fingers of the operator as will be described more fully below. The barrel 20 also has a counter bore 24 in the end adjacent the flange 21 which terminates in shoulder 24a and which permits reception of an extension of the body 30 of the syringe, as also will be described in greater detail below.

Finally, the barrel has a radial opening 23 which leads to a fitting 23a which is intended to receive a flexible tubing 25. This tubing 25 has a conventional snap fitting 26 on one end and is intended to be secured to a vacuum source for aspirating purposes. To facilitate use of the syringe, a double loop retainer 90 is provided. This retainer can be slipped over syringe body 30 and engages tubing 25 as shown in FIG. 2. In this fashion the tubing will not interfere with the operator's movements.

The syringe body 30 is also an elongate, cylindrical member having a reduced diameter projection 32 on one end. This projection is intended to be telescopically fit into the counter bore 24 of the barrel 20 to seat against shoulder 24a, as is clearly shown in FIG. 3. The syringe body 30 also has a shoulder 34 at the point where projection 32 joins the main body which fits against the outer surface of the flange of the barrel 20 so that the body 30 can be secured to barrel 20 and securely lodged against the end thereof. The opposed end of the body 30 terminates in a circumferential flange 31 for purposes which will be described below.

Received interiorally of the body 30 is a spring housing 60, which is essentially cylindrical in configuration and has an annular reverse flange 62 on its inboard end which forms a seat 62a for receipt of one end of coil spring 63. A bushing 64 is also provided adjacent to the inboard end of the spring housing 60.

The spring housing also has a circumferential flange 61 on its opposed end which seats on the flange 31 of the body 30 of the syringe when the housing has been inserted into the body.

A plunger means 70 is received centrally of the spring housing, with the second end of the spring 63 bearing against the head 71 on the plunger. In this fashion the normal pressure of the spring will urge the plunger to the outboard position such as is shown in FIG. 3.

The plunger is an elongate cylindrical member having, as noted before, a head 71 on one end thereof intended to be contacted by the thumb of the operator and a shoulder 73 spaced a short distance therefrom which will seat on the outboard end 62b of the return flange 62 of the spring housing 63 to limit the degree of penetration of the plunger means.

The plunger body is elongate in nature and has longitudinal slits 72,72 at the opposed end thereof dividing it into fingers 74,75. These slits enable the plunger body at its inboard end to expand and contract for purposes of contacting the detents on the drive shaft 80, which will now be described.

The drive shaft member 80 is received interiorally of the plunger body 70 and is an elongate member with a generally circular cross section having an outboard end 83 and an inboard end 81. A pointed projection 84 is received on the inboard end 81 of the drive shaft 80 and is intended to engage the rear seal 53 of cartridge 50 upon depression of the plunger. This projection is intended to pierce and engage the rear seal or plug 53 of the cartridge and will thereby insure that plug 53 and drive shaft 80 will retain their axial positions after each actuation of the device, notwithstanding any tendency of the plunger to pull them rearwardly.

It should be noted at this point that there are plungers or drive members in this art having barbed points on their ends. They, however, are intended to engage the seal of the cartridge and retract the seal, which is the opposite effect desired in this instance.

An O-ring 85 is also disposed in a groove 84a on the end of the drive shaft for sealing and locating purposes. The remaining body of the drive shaft has a plurality of shoulders 82,82 disposed along its length which serve as detent means in conjunction with the fingers 74,75, of the plunger body. These detents are of predetermined length and serve to control the amount of inward movement of the drive shaft with each depression of the plunger, as will be described.

Completing the assembly is a locking ring 64 which is telescoped over the body of the plunger 70. This ring 64 frictionally engages the body and has two inwardly projecting members 64a,64a which engage the slots 72,72 of the body to retain the same in precise alignment and to minimize any tendency of the body to rotate about its longitudinal axis.

In use or operation of the improved device, and assuming it to be assembled as shown in FIG. 3 of the drawings, it will first be noted that an aspirating capability is present. It will be noted that the suction tube 25 communicates with the interior of the barrel 20 through opening 23. This is adjacent the needle 40 and is forward of the front end of the cartridge 50. In this fashion and due to the O-ring seal 52 between the cartridge and the interior surface of the barrel, a closed chamber is provided so that a complete aspiration can be achieved without any contamination or risk of contamination of the contents of the cartridge 50.

Once it is desired to seat the cartridge on the end of the needle 40, the syringe is grasped with two fingers engaging flange 21 and the thumb on the head 71. Following this, it is merely necessary to push the plunger 70 in the direction of the arrow 100. This will first engage the point 84 with the rear seal 53 of the cartridge. This will seat also the cartridge on the end of the needle and also seal off the vacuum source to prevent any further aspirating effect.

Upon further depression of the plunger 70, it should be noted that the plunger can only advance until its shoulder 73 seats on shoulder 62b of the spring housing 60. The drive shaft, of course, will move in the direction of arrow 100, and the fingers 74,75 of the plunger will grip the first detent 82.

When the plunger is pushed, the fingers 74 and 75 will grip a detent on a drive shaft and urge it forward the same distance that the plunger travels. This will, of course, force the rear plug 53 a predetermined distance along the axis of the cartridge and will result in dispensing or injecting a predetermined measure of fluid.

When the plunger is released, the detent gripping fingers 74 and 75 will open, permitting the force of the spring 63 to force the plunger back to the position shown in FIG. 2. The pointed projection 84 will retain the drive shaft in contact with the rear seal 53 of the cartridge and resist any back pull from fingers 74 and 75. Successive operations of the plunger will result in this operation being repeated, and in each instance the plug 53 will be advanced a predetermined distance based upon the detent spacing. Again, a predetermined regulated amount will be dispensed in each instance.

Accordingly, several advantages are believed to be achieved by the aforementioned construction.

First of all, if a local anesthetic is being used, it is vital not to inject it directly into a blood vessel. This is controlled because of the fact that the design of the syringe makes it possible to very easily and accurately control the location of the same. In other words, a needle can be securely and accurately held in its proper location.

Furthermore, provision of the O-ring on the cartridge and the relative relationship of the opening 23 in the barrel permit complete and safe aspiration.

Additionally, the detent-type drive shaft, in cooperation with the fingers on the plunger, permit a positive control or check on the rate and amount of flow of the material being injected. This makes it possible to inject only measured amounts and also makes it possible to inject at a measured rate so as to avoid a premature injection of the complete contents of the cartridge.

While a full and complete description of the invention has been set forth in accordance with the dictates of the Patent Statutes, it should be understood that modifications can be resorted to without departing from the spirit hereof or the scope of the appended claims.

What is claimed is:

1. A syringe adapted to receive a cartridge internally thereof, comprising;
   A. an elongate hollow body having first and second ends;
   B. an elongate hollow barrel having first and second ends;
   C. said first end of said body being releasably connected to said second end of said barrel in coaxial relationship therewith;
   D. plunger means received within said second end of said body in coaxial alignment therewith and being movable along the longitudinal axis thereof;
   E. an elongate cartridge having
      1. first and second ends and front and rear seals on said first and second ends, respectively, and
      2. being received in said barrel in coaxial alignment therewith, with said second end disposed adjacent said second end of said barrel;
   F. metering means received within said body in coaxial alignment therewith;
   G. means for engaging said rear seal of said cartridge carried by the end of said metering means disposed adjacent thereto;
   H. said plunger being releasably engagable with said metering means;
   I. said metering means being movable a predetermined distance in one direction along the axis of said body and said barrel in response to movement of said plunger means
      1. whereby a measured amount of contents of said cartridge will be ejected upon depression of said plunger; and
   J. vacuum means carried by said first end of said barrel in fluid communication therewith.

2. The syringe of claim 1 wherein
   A. said metering means include an elongate drive shaft having a series of radially extending shoulders along its length; and
   B. gripping means are carried by one end of said plunger means and adapted to releasably engage said shoulders.

3. The syringe of claim 1 wherein
   A. said plunger is spring-loaded and normally urged to an extended position with respect to said second end of said body; and
   B. limiting means are carried internally of said body for engagement with said plunger
      1. whereby the extent of depression of said plunger against the force of said spring is controlled.

4. The syringe of claim 1 wherein
   A. said means for engaging said rear seal of said cartridge are needle-like and are carried on said metering means for frictional engagement with said rear seal of said cartridge
      1. whereby said metering means and said rear seal will retain their positions upon movement of said plunger in the opposite direction.

5. The syringe of claim 1 wherein
   A. a needle is carried by said first end of said barrel;
   B. said vacuum means are secured to said barrel adjacent said needle in fluid communication with the interior thereof; and
   C. means are provided between said first end of said cartridge and said first end of said barrel for sealing off the end of said barrel for aspirating purposes.

6. A syringe adapted to receive a cartridge having first and second seals, comprising;
   A. an elongate hollow body;
   B. an elongate hollow barrel
      1. one end of which is releasably connected to one end of said body in coaxial relationship therewith;
   C. a cartridge received within said barrel with its first seal located adjacent the end of said barrel which is connected to said body;
   D. metering means
      1. carried internally of said body and said barrel,
      2. being movable along the longitudinal axis thereof and
      3. one end of which is adapted to engage said first seal of said cartridge;
   E. spring loaded plunger means carried by the opposed end of said body and being movable along the longitudinal axis thereof;
   F. gripping means carried by said plunger means for movement therewith and releasably engagable with said metering means;
   G. axially extending needle-like engagement means carried one the opposed end of said barrel and being engageable with said second seal of said cartridge upon movement of said plunger means; and
   H. vacuum means carried by said barrel adjacent said needle means in fluid communication with the interior of said barrel.

7. The syringe of claim 6 wherein said metering means include
   A. an elongate shaft having
      1. first and second ends, with said first end being disposed adjacent said first seal of said cartridge
      2. a plurality of radially extending shoulders spaced along its length and
      3. a needle like seal-engaging member disposed on said first end.

8. The syringe of claim 7 wherein said gripping means of said plunger means include
   A. opposed axially extending fingers adapted to releasably engage said shoulders of said drive shaft.

9. The device of claim 6 wherein
   A. limiting means are carried internally of said body; and
   B. said plunger means are movable into and out of engagement with said limiting means.

* * * * *